(12) United States Patent
Drewnowski

(10) Patent No.: US 12,102,079 B2
(45) Date of Patent: Oct. 1, 2024

(54) GAS MONITORING DEVICE AND METHOD

(71) Applicant: Degesch America, Inc., Richmond, VA (US)

(72) Inventor: Bartek P. Drewnowski, Richmond, VA (US)

(73) Assignee: DEGESCH AMERICA, INC., Richmond, VA (US)

(*) Notice: Subject to any disclaimer, the term of this patent is extended or adjusted under 35 U.S.C. 154(b) by 996 days.

(21) Appl. No.: 17/025,315

(22) Filed: Sep. 18, 2020

(65) Prior Publication Data

US 2021/0076661 A1 Mar. 18, 2021

Related U.S. Application Data

(60) Provisional application No. 62/901,850, filed on Sep. 18, 2019.

(51) Int. Cl.
A01M 13/00 (2006.01)
A23B 9/22 (2006.01)
G01M 3/00 (2006.01)

(52) U.S. Cl.
CPC ............... *A01M 13/00* (2013.01); *A23B 9/22* (2013.01); *G01M 3/00* (2013.01)

(58) Field of Classification Search
CPC ..................................................... A01M 13/00
See application file for complete search history.

(56) References Cited

U.S. PATENT DOCUMENTS

| 4,309,897 | A  | 1/1982  | Springer et al. |
| 6,252,510 | B1 | 6/2001  | Dungan |
| 6,885,309 | B1 | 4/2005  | Van Heteren |
| 6,947,138 | B2 | 9/2005  | Arno |
| 7,504,068 | B2 | 3/2009  | Lehmann et al. |
| 8,247,775 | B2 | 8/2012  | Patel et al. |
| 8,586,383 | B2 | 11/2013 | Walte et al. |

(Continued)

FOREIGN PATENT DOCUMENTS

| CN | 203216526 U | 9/2013 |
| CN | 206440701 U | 8/2017 |

(Continued)

OTHER PUBLICATIONS

English Translation of CN 108458755 A provided by espacenet.com: Lni, Pu et al.; Raw Material Storage Environment Monitor with Fumigating and Air Guiding Functions; Aug. 28, 2018 (Year: 2018).*

(Continued)

*Primary Examiner* — Kevin Joyner
(74) *Attorney, Agent, or Firm* — MILLEN, WHITE, ZELANO & BRANIGAN, P.C.; Ross J. Christie

(57) ABSTRACT

The present invention relates to a gas monitoring device having a gas tight base unit containing a sensor. The base unit is detachably connected to an elongated hollow rod having a perforated tip end and a base unit connection end. The base unit comprises a sensor, a data processor, a telemetry unit, a battery with wireless charging and an internal on/off switch. The invention also relates to a method of monitoring the gas concentration within a fumigated commodity sample comprising inserting the tapered perforated end of a gas monitoring device into a commodity sample.

18 Claims, 14 Drawing Sheets

(56) References Cited

U.S. PATENT DOCUMENTS

| | | |
|---|---|---|
| 8,623,189 B2 | 1/2014 | Eckhardt et al. |
| 9,551,683 B2 | 1/2017 | Ishibashi et al. |
| 9,945,806 B2 | 4/2018 | Eckhardt et al. |
| 10,106,403 B2 | 10/2018 | Mayne-L |
| 10,296,863 B2 | 5/2019 | Bantas et al. |
| 10,330,617 B2 | 6/2019 | Hur et al. |
| 2004/0056771 A1 | 3/2004 | Dungan |
| 2007/0131550 A1 | 6/2007 | Mizutani et al. |
| 2008/0277586 A1 | 11/2008 | Cardinale |
| 2010/0252451 A1 | 10/2010 | Warburton |
| 2015/0177206 A1 | 6/2015 | Basham et al. |
| 2016/0139096 A1 | 5/2016 | Glennon |
| 2017/0212100 A1* | 7/2017 | Kwak ............... A61B 5/082 |
| 2018/0266985 A1 | 9/2018 | Farhad |
| 2018/0322436 A1* | 11/2018 | Sotiroudas ......... G01N 33/0075 |
| 2019/0079041 A1 | 3/2019 | Sinitskii et al. |
| 2019/0265082 A1 | 8/2019 | Zafar et al. |

FOREIGN PATENT DOCUMENTS

| | | | |
|---|---|---|---|
| CN | 107271227 A | 10/2017 | |
| CN | 108458755 A * | 8/2018 | ............ A01M 13/00 |
| KR | 859031 B1 | 9/2008 | |
| WO | 20104750 A1 | 5/2020 | |

OTHER PUBLICATIONS

International Search Report PCT/US2020/51435 dated Feb. 2, 2021 (p. 1).

Brabec et al. "Evaluation of Wireless Phosphine Sensors for Monitoring Fumigation Gas in Wheat Stored in Farm Bins" Insects, vol. 10 Issue 5 (Apr. 27, 2019): pp. 1-11.

Agrafiotl et al. Modeling the distribution of phosphine and insect mortality in cylindrical grain silos with Computational Fluid Dynamics: Validation with field trials Computers and Electronics in Agriculture, vol. 173 (Apr. 9, 2020): pp. 1-11.

* cited by examiner

FIG. 3B
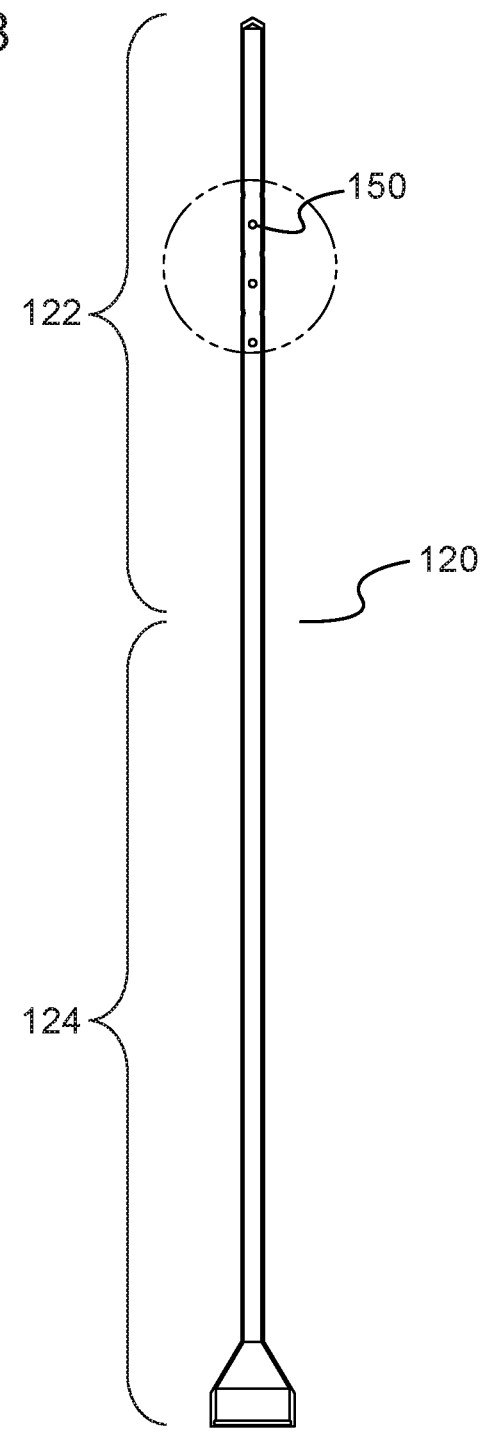
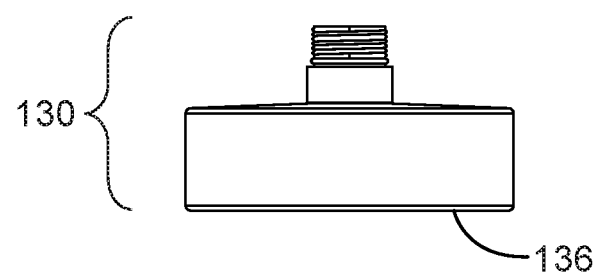

GAS MONITORING DEVICE AND METHOD

This application claims priority of U.S. Patent Application No. 62/901,850 filed Sep. 18, 2019, the entirety of which is incorporated herein by reference.

BACKGROUND

Typically upon harvest, an agricultural commodity is placed in jute bags, boxes and/or stored in large enclosures, such as sheds, warehouses, or silos. Agricultural commodities after harvest are often infested with insects that can consume or damage substantial amounts of the commodity.

One approach to prevent these losses is to fumigate the commodity during storage and/or immediately prior to or after shipping.

Gas fumigants have been used for decades for disinfesting closed environments infested with or suspected to be infested with insect pests such as weevils, bugs, moths and cockroaches, either mature or in various larval stages or in the form of eggs. Such fumigation is particularly used for the disinfestation of agricultural bulk commodities such as, for example, non-food commodities, processed foods, raw commodities and fresh commodities.

Phosphine ($PH_3$) has been a preferred gaseous fumigant for stored grain and similar particulate commodities because any residue of the fumigant will be lost or oxidized to a harmless phosphate when the grain or other commodity is processed to produce a food. Examples of the fumigation of grain with phosphine are found in the specifications of, for example, WO91/00017; U.S. Pat. Nos. 4,059,048; 4,200,657; 4,756,117; 4,812,291; 5,411,704 and 10,296,863. The entire teachings and disclosures of which are incorporated by reference herein.

The phosphine concentration pattern with the fumigation enclosure area can be influenced by, for example, temperature, air pressure and humidity. Phosphine gas concentration initially rises more or less steeply up to a maximum and from there drops asymptotically to zero at a rate which depends on phosphine losses due to leakage, decomposition or other causes. In extreme cases this may result in the phosphine concentration dropping so rapidly that complete killing of the pests, in particular their pre-adult stages, cannot be ensured. As a general rule it is preferred in phosphine fumigation to maintain lethal pesticidal gas concentrations as constantly as possible over a prolonged fumigation period. A skilled worker can refer to the teachings of U.S. Pat. No. 10,296,863 which discloses conventional calculations of air properties, boundary conditions, mass convective boundary conditions, optimization of fumigant dosage and treatment duration, how to account for gas flow within porous media, insect mortality in relation to gas levels, and various other models for estimating effective gas concentrations. The entire teachings and disclosures of U.S. Pat. No. 10,296,863 are incorporated by reference herein.

Accordingly, it would be desirable to be able to regulate the phosphine gas concentration pattern during fumigation and to maintain the desired lethal concentrations or pattern of concentrations over a prolonged period of fumigation by the controlled addition of fumigant gas.

Phosphine gas sensors serve to monitor the phosphine concentration in the enclosed fumigation area to ensure exposure sufficient to eradicate unwanted pests. Typically phosphine gas is circulated through the stored commodity either by the natural convection currents that are present in the storage area or by active recirculation of air through the commodity using, for example, recirculation ducts. Examples can be found in, for example, U.S. Pat. Nos. 4,200,657 and 4,756,117. However, some commodities are very densely packed which creates an insulation effect whereby air/gas currents do not equally penetrate the interior of the commodity container. The air/gas circulation within the inner most areas of a densely packed commodity container can be significantly lower than the air/gas flow in the outer areas of a densely packed commodity container. Thus, the concentration of phosphine gas reaching the densely packed inner storage areas is often insufficient for the complete killing of pests. The industry has attempted to monitor the interior regions of a commodity container by means of gas sampling. However, this is problematic as negative pressures are created by the sampling pumps within the commodity container.

Some commercial sensors are designed to be inserted into the stream during commodity loading resulting in random placement of the sensor within the bin/truck/container. This is problematic as there is no way to retrieve the sensor to service or charge. It is also very problematic if the sensor is lost in the grain or commodity mass and is inadvertently introduced into the supply chain. A loose chip from a damaged or fragmented sensor could contaminate an entire batch of commodity resulting in substantial loss.

Thus, the need exists to monitor the supply of phosphine to all regions of the bulk stored commodity in levels sufficient to eradicate unwanted pests. Moreover, phosphine gas is very corrosive and tends to quickly degrade or corrode electronics. Thus, the need exists for a phosphine sensor in which the electronic components are housed within an airtight sealed environment. A goal of the present invention is to provide a sensor which is able to accurately measure the gas concentration with an interior region of a bulk stored commodity. A further goal of the present invention is to provide a sensor which is able to accurately measure the gas concentration with an ambient environment. A further goal of the present invention is to provide a sensor which is able to accurately measure the gas concentration with an ambient environment and within the interior region of a bulk stored commodity. A further goal of the present invention is to provide a phosphine sensor device that is protected from the corrosive effects of the phosphine gas. A further goal of the present invention is to provide a method a gaining access/space to place a sensor within the inner areas of a sealed commodity container. Upon further study of the specification and appended claims, further goals, objects and advantages of this invention will become apparent to those skilled in the art.

BRIEF SUMMARY OF INVENTION

One embodiment of the present invention relates to a gas monitoring device comprising a gas tight base unit containing a sensor. The base unit is detachably connected to an elongated hollow rod. The base unit comprise a sensor, data processor, a telemetry unit, a battery with wireless charging and an internal on/off switch. The elongated hollow rod has a perforated tip end and a base unit connection end. Preferably, the elongated hollow rod end is between 12 to 36 inches long. Preferably, the perforated tip end is in the shape of a spike. Preferably, the base end is 4 to 10 inches wide and 2 to 6 inches tall. Preferably, the housing unit is made of a shock absorbing plastic.

A further embodiment of the present invention relates to a gas monitoring device comprising a perforated sensor tip detachably connected to a gas tight housing unit having a rod end and a base end. The base end comprise a data processor, a telemetry unit, a battery with wireless charging and an internal on/off switch. The sensor tip contains a gas sensor and optional filter media. The rod end contains a gas tight plug through which a connecting wire connects the sensor to the data processor in the base end. The rod end is narrower than the base end. Preferably, the elongated rod end of the housing is between 12 to 36 inches long. Preferably, the rod end is between 0.5 to 1 inch in diameter. Preferably, the perforated sensor tip is between 0.5 and 2 inches long. Preferably, the base end is 4 to 10 inches wide and 2 to 6 inches tall. Preferably, the housing unit is made of a shock absorbing plastic.

A further embodiment of the present invention relates to a two piece commodity probe comprising a hollow outer sleeve with a tapered wall at a first end and a collar on a second end and a removable inner core with a spike on a first end and a collar on a second end. The inner core fits within the hollow outer sleeve and the spike extends beyond the tapered wall at the first end of said outer sleeve. See, for example, FIG. 7.

A further embodiment of the present invention relates to a method of monitoring the gas concentration within a fumigated commodity sample comprising inserting the elongated hollow rod into a commodity sample. See, for example, FIGS. 2, 8 and 9. The method advantageously does not require external gas sampling pumps. External gas sampling is often problematic and results in unreliable concentration data. As seen in FIG. 2, the perforated tip end of the elongated hollow rod end acts as a spike to enable entry into the interior portion of a commodity container.

Preferably, the gas monitoring method of the present invention measures phosphine gas concentration in parts per million. The data is collected and transmitted via a telemetry based communication unit at preset intervals and sent to cloud storage and/or cell phone.

BRIEF DESCRIPTION OF THE DRAWINGS

Various features and attendant advantages of the present invention will be more fully appreciated as the same becomes better understood when considered in conjunction with the accompanying drawings, in which like reference characters designate the same or similar parts throughout the several views, and wherein:

FIG. 3b depicts an embodiment of a gas monitoring device according to the present invention where the elongated hollow rod is detached from the base end (130).

DETAILED DESCRIPTION

Figure 1:
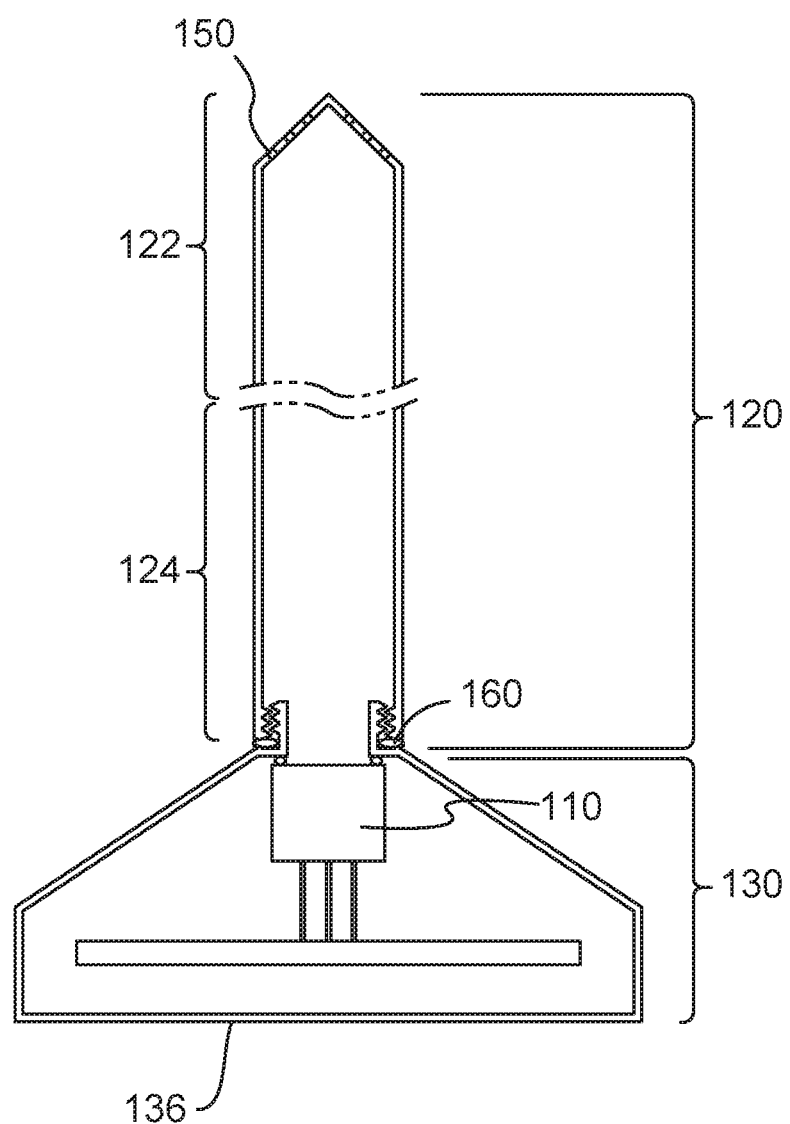
FIG. 1 depicts an embodiment of a gas monitoring device according to the present invention (not to scale).

As used herein the term "perforations" or "perforated" refers to openings which allows airflow to reach the interior of the elongated hollow rod. They can be any size and shape (e.g., slots, holes, ovals, squares) which allow air into the interior of the elongated hollow rod to reach the sensor in the base unit. Preferably, the perforations are within the tip end of the elongated hollow rod which is about the top 50% of the elongated hollow rod.

Particularly in embodiments where the sensor is in the tip, the perforations can be any size and shape (e.g., slots, holes, ovals, squares) which allow the sensor tip to be protected while still allowing air to reach the sensor. Several contemplated variations are depicted in FIGS. 11a, 11b, 11c, 11d and 11e.

As used herein the term "Commodity container" refers to an enclosed environment containing stored commodities (e.g., vertical storage, tanks, flat storage (loose construction), farm bins, bunkers, tarped ground storages, railcars, barges, ship-holds, mills, warehouses, chambers, or silos). Commodity container can also include sub-containers stored with a larger enclosed environment such as, for example, cartons, wooden barrels, jute bags, woven bags, woven poly, supersack, bales, mesh bags, paper bags and/or plastic/poly bags.

Typical commodities requiring fumigation include, for example, non-food commodities, processed foods, raw commodities and fresh commodities.

Non-food Commodities include, for example, processed or unprocessed cotton, wool and other natural fibers or cloth, clothing; straw and hay; feathers, human hair, rubberized hair, vulcanized hair, mohair, leather products, animal hides and furs, tobacco, tires (for mosquito control), wood, cut trees, wood chips, wood products, bamboo products, paper, paper products, *psyllium* seed, *psyllium* seed husks, dried plants, flowers, seeds (such as grass seed, ornamental herbaceous plant seed and vegetable seed).

Processed food commodities include, for example, processed candy and sugar, cereal flours and bakery mixes, cereal foods (including cookies, crackers, macaroni, noodles, pasta, pretzels, snack foods and spaghetti), processed cereals (including milled fractions and packaged cereals), cheese and cheese byproducts, chocolate and chocolate products (such as assorted chocolate, chocolate liquor, cocoa, cocoa powder, dark chocolate coating and milk chocolate products), processed coffee, corn grits cured meat products, dried fish, dates, figs, dried eggs, egg yolk solids, dried milk, dried powdered milk, non-dairy creamers, non-fat dried milk, dried or dehydrated fruits (such as apples, dates, figs, peaches, pears, prunes, raisins, citrus and sultanas), processed herbs, spices, seasonings, condiments, malt, processed nuts (such as almonds, apricot kernels, brazil nuts, cashews, filberts, macadamia nuts, peanuts, pecans, pistachio nuts, walnuts and other processed nuts), processed oats (including oatmeal), rice (brewer's rice, grits, enriched and polished), soybean flour and milled fractions, processed tea, dried and dehydrated vegetables (such as beans, carrots, lentils, peas, potato flour, potato products and spinach), yeast (including primary yeast) wild rice and other processed foods.

Raw Commodities include, for example, almonds, animal feed & feed ingredients, barley, brazil nuts, cashews, cocoa beans, coffee beans, corn, cottonseed, dates, filberts, flower seeds, grass seeds, legume vegetables (dried), millet, oats, peanuts, pecans, pistachio nuts, popcorn, rice, rye, safflower seeds, sesame seeds, sorghum, soybeans, sunflower seeds, triticale, vegetable seeds, walnuts and/or wheat.

Fresh commodities include, for example, alfalfa, avocado, banana (including plantains), cabbage, citrus, citron, dill, eggplant, endive, grapefruit, kumquat, legume vegetables (succulent), lemon, lettuce, lime, mango, okra, orange, papaya, pepper, persimmon, pimento, salsify tops, sweet potato, tangelo, tangerine and/or tomato.

FIG. 1 depicts a preferred embodiment of the present invention (not to scale). The gas monitoring device comprises a gas tight base unit (130) containing a sensor (110). The base unit is detachably connected to an elongated hollow rod (120) having a tapered tip end (122) and a base connection end (124). The base unit comprise a sensor (110), data processor, a telemetry unit, a battery with wireless charging and an internal on/off switch. Preferably, the elongated hollow rod end is between 12 to 36 inches long. Preferably, the perforated tip end is in the shape of a spike. Preferably, the base end is 4 to 10 inches wide and 2 to 6 inches tall. Preferably, the housing unit is made of a shock absorbing plastic. In certain embodiments the base unit may contain one or more additional sensors to detect various other environmental conditions.

Figure 6:
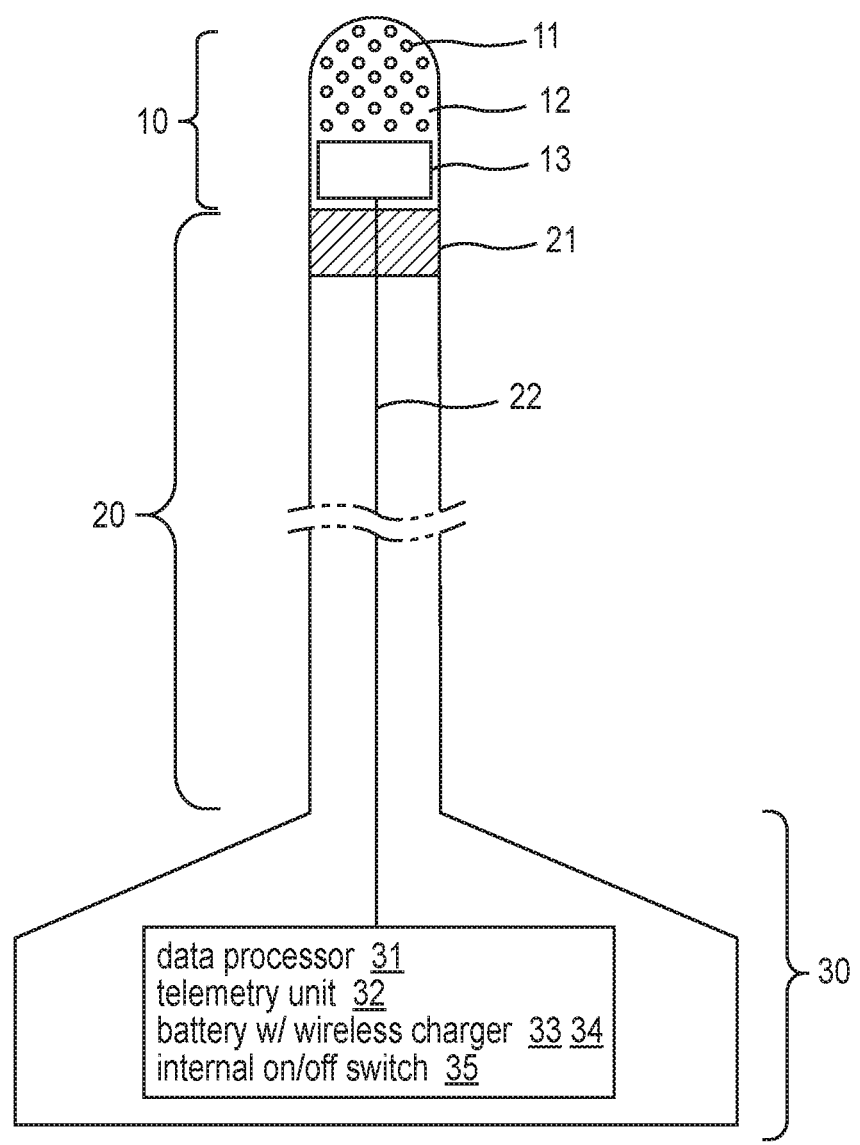
FIG. 6 depicts an embodiment of a gas monitoring device according to the present invention in which the sensor is in the tip end.

FIG. 6 depicts another preferred embodiment of the present invention, a gas monitoring device comprising a perforated sensor tip (10) detachably connected to a gas tight housing unit having a rod end (20) and a base end (30). The base end houses a data processor (31), a telemetry unit (32), a power supply (e.g., battery (33) with wireless charging (34)) and an internal on/off switch (35). The sensor tip (10) contains a gas sensor (13) and optional filter media (12). In certain embodiments the sensor tip may contain the one or more additional sensors to detect various other environmental conditions. Preferably, the gas sensor is a phosphine high range sensor (0-2000 ppm) located within a rounded or domed perforated tip. However, the top of the tip may be flat, domed, pointed etc. The perforations may be any shape which allow air/gas to circulate and reach the sensor. FIGS. 11a-11e depicts several contemplated variations for the shape of the sensor tip and the shape of the openings within the sensor tip. For example, the perforations may be slots, holes, ovals, squares etc. The perforations may also be a combination of shapes. In a preferred embodiment filter media covers the sensor to protect the sensor from dust or particulate matter. The rod end (20) contains a gas tight plug (21) through which a connecting wire (22) operably connects the sensor (13) to the data processor (31) in the base end (30) of the housing unit. The rod end (20) is narrower than the base end (30). Preferably, the elongated rod end of the housing unit is between 18 to 32 inches long. Most preferably, the elongated rod end of the housing unit is between 22 to 25 inches long. The rod end (20) is generally between 0.5 to 1.5 inches in diameter. Preferably, the rod end is between 0.5 to 1 inches in diameter. Most preferably, the rod end is between 0.5 to 0.8 inches in diameter. Generally, the perforated sensor tip (10) is between 0.3 and 2 inches long. Preferably, the perforated sensor tip is between 0.4 and 1.25 inches long. Most preferably, the perforated sensor tip is between 0.5 and 1 inches long. The device can advantageously measure phosphine concentrations from ambient air or commodity phosphine concentrations from within the inner areas of a fumigated commodity container without the use of external mechanical sampling pumps.

The telemetry unit (32) transmits collected data via wireless data transfer mechanisms (e.g., using radio RFID, ultrasonic, infrared systems, cellular telephone networks (e.g., GSM networks using SMS)).

Figure 10:
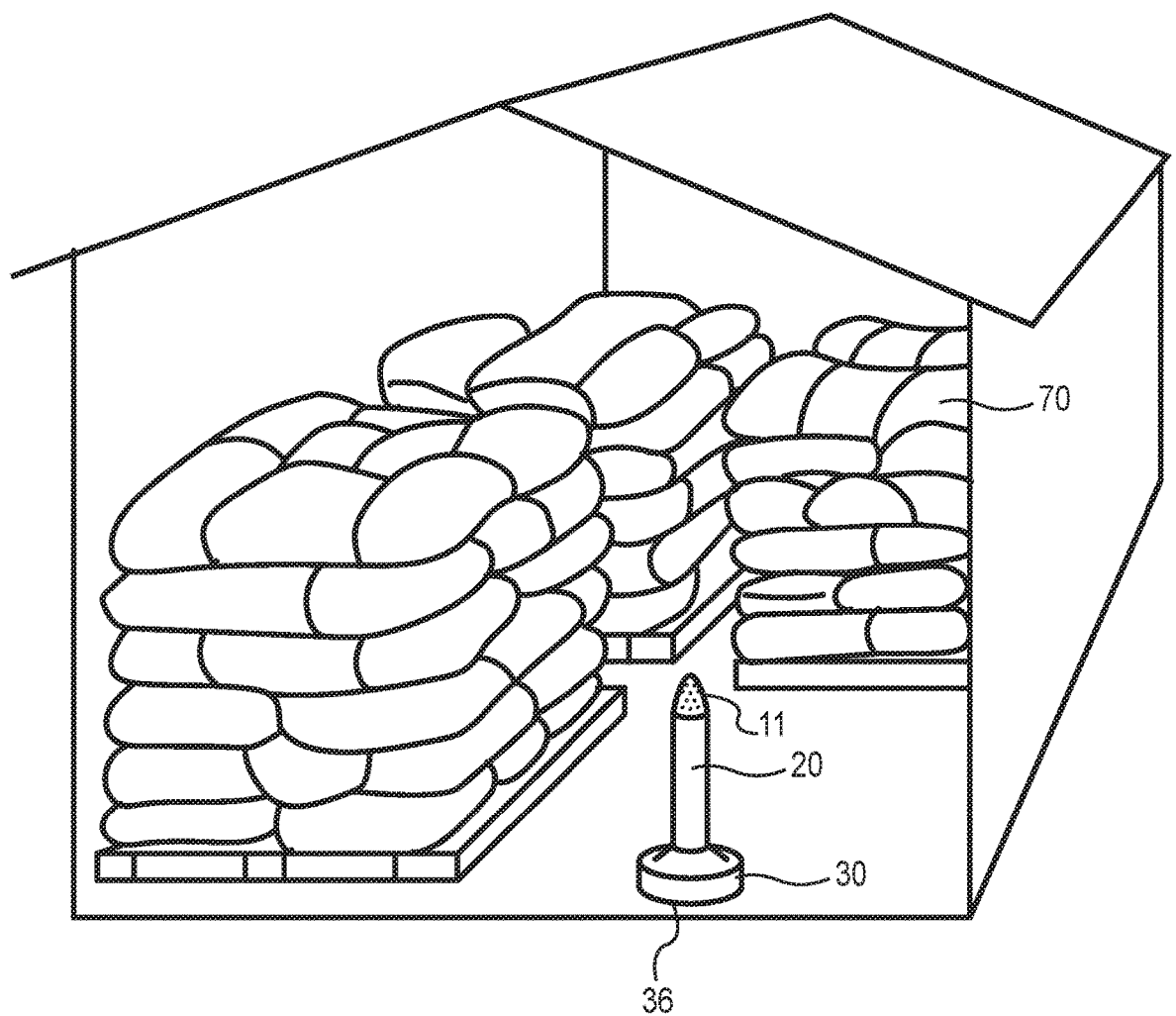
FIG. 10 depicts an embodiment of a gas monitoring device according to the present invention placed with an enclosed environment containing stored commodities. The unit is free-standing when the bottom (36) of the base end (30) is placed on a solid support.
Figure 11A:
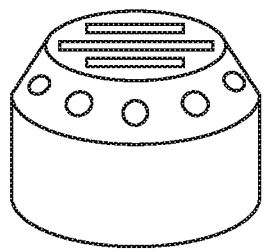
FIG. 11a depicts a sensor tip embodiment of the gas monitoring device according to the present invention.
Figure 11B:
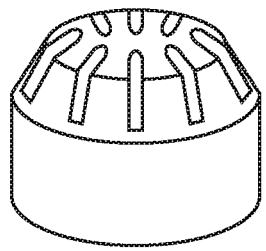
FIG. 11b depicts a sensor tip embodiment of the gas monitoring device according to the present invention.
Figure 11E:
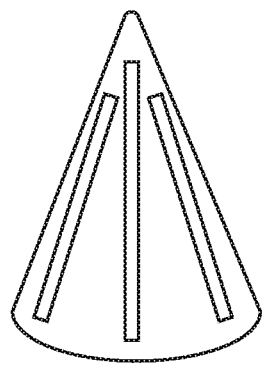
FIG. 11e depicts a sensor tip embodiment of the gas monitoring device according to the present invention.
Figure 11C:
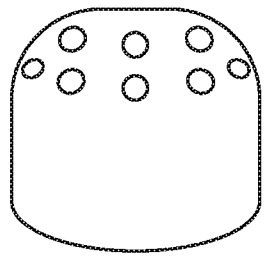
FIG. 11c depicts a sensor tip embodiment of the gas monitoring device according to the present invention.
Figure 11D:
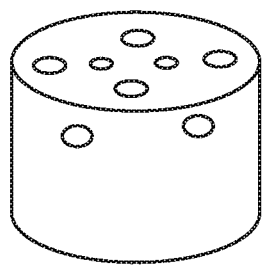
FIG. 11d depicts a sensor tip embodiment of the gas monitoring device according to the present invention.

In preferred embodiments the gas monitoring device stands between about 22 to 38" tall. The tapered end of the elongated rod is a perforated which allows for air/gas movement within the space. The elongated rod is detachably removable from the base. Thus, in certain environments it is desirable to place a removable filter medium within the rod so that it sits above, or adjacent the sensor contained within the base. The filter will protect the sensor from particulate matter and solid dust particles. The sensor operably connects to the board of the data processor (131) located in the base end (130). The base end is preferably 4" to 10" wide and 2" to 6" tall with a wall sloping inward towards the juncture with the rod end forming a cone shaped round base. In a preferred embodiment the base is adapted to support the device in a free-standing upright position such as depicted in FIG. 10. The base end will house electronics (e.g., battery, on/off switch, data processor, telemetry unit, power indicator, wireless charger). During manufacturing of the device the components are operably connected and installed within the base unit. After installation a bottom plate will be sealed into position on the bottom of the base end. In preferred embodiments the housing of the device will be made of molded shock absorbing plastic. It is also preferred that the housing be of high visibility colors such as, for example, orange. The housing may also contain high visibility markings such as reflective strips or patches. Preferably, high visibility markings are placed on the base unit.

Figure 3:
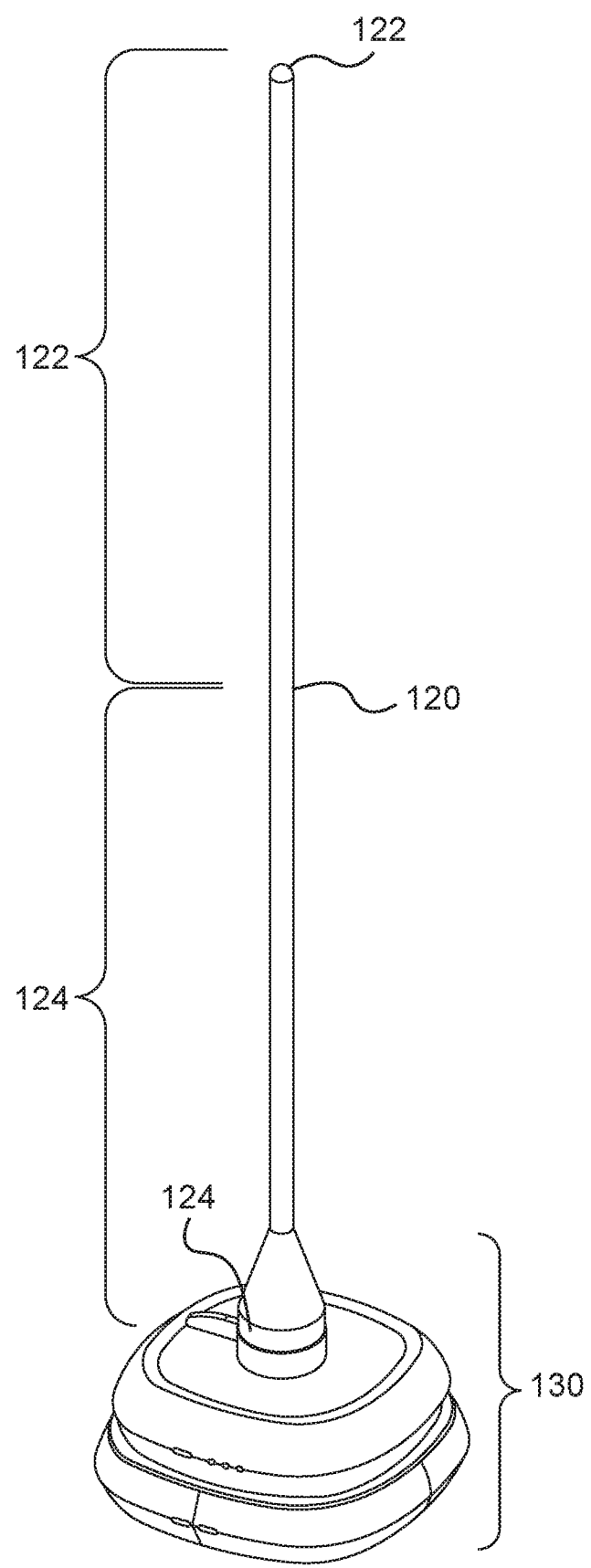
FIG. 3 depicts an embodiment of a gas monitoring device according to the present invention which is free-standing when the base end (130) is placed on a solid support.
Figure 3A:
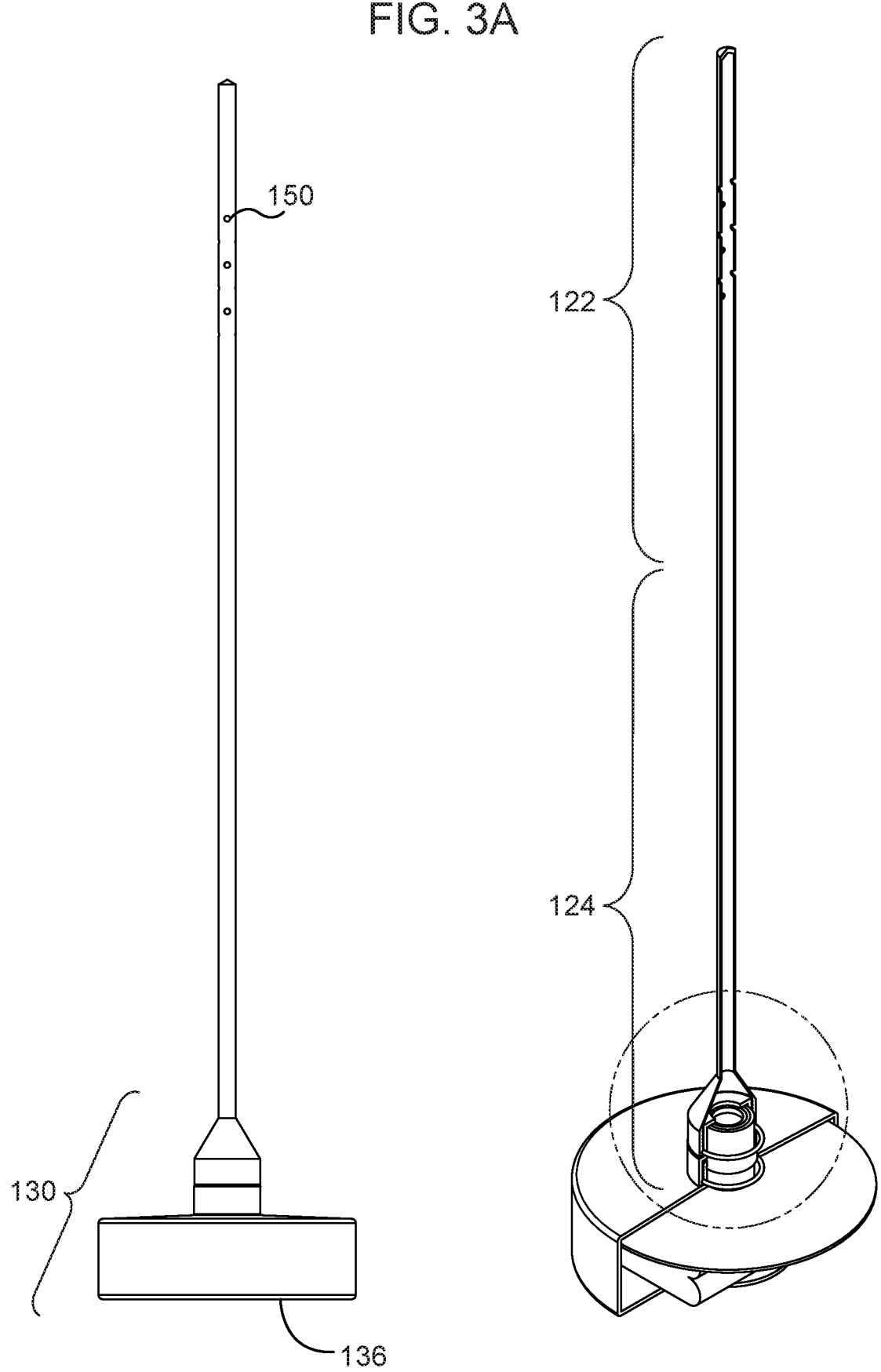
FIG. 3a depicts an embodiment of a gas monitoring device according to the present invention which is free-standing when the bottom (136) of the base end (130) is placed on a solid support.
Figure 3C:
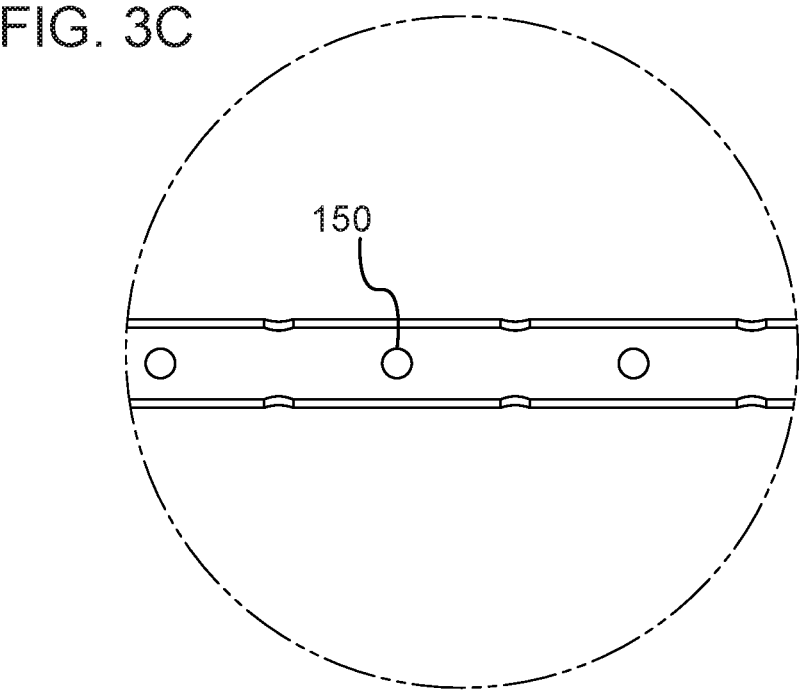
FIG. 3c depicts a detail close up view of the tip end of an embodiment of an elongated hollow rod according to the present invention. Perforations are spaced along the top portion of the tip end of the elongated hollow rod.
Figure 3D:
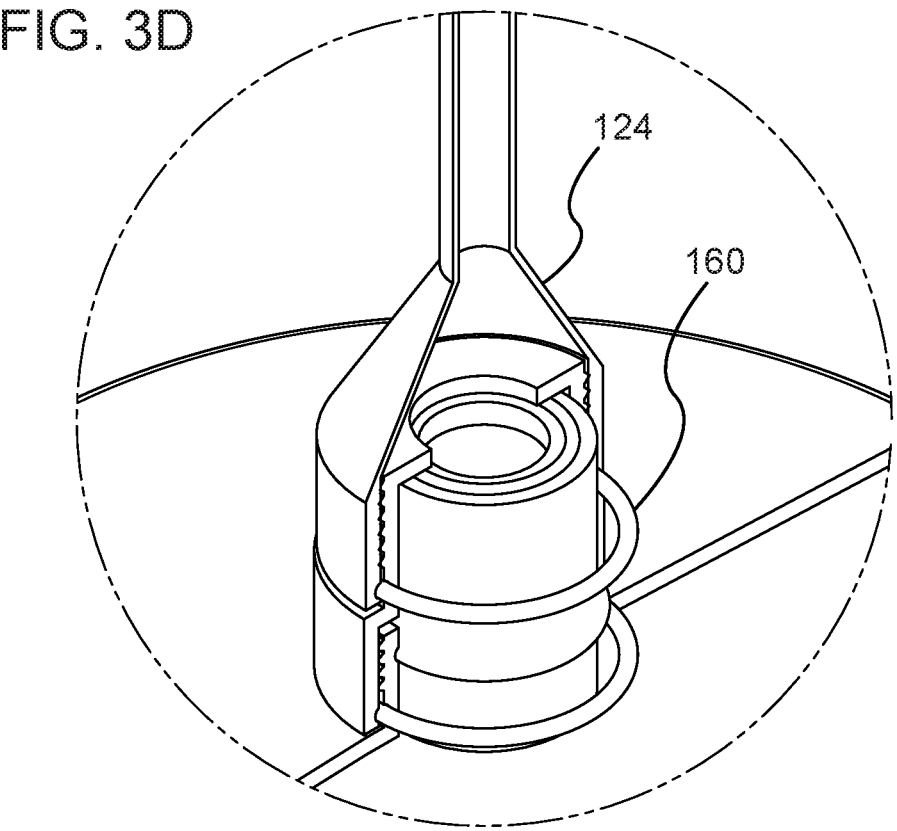
FIG. 3d depicts a detail close up view of o-ring seals within the connection between the base unit and the elongated hollow rod.
Figure 4:
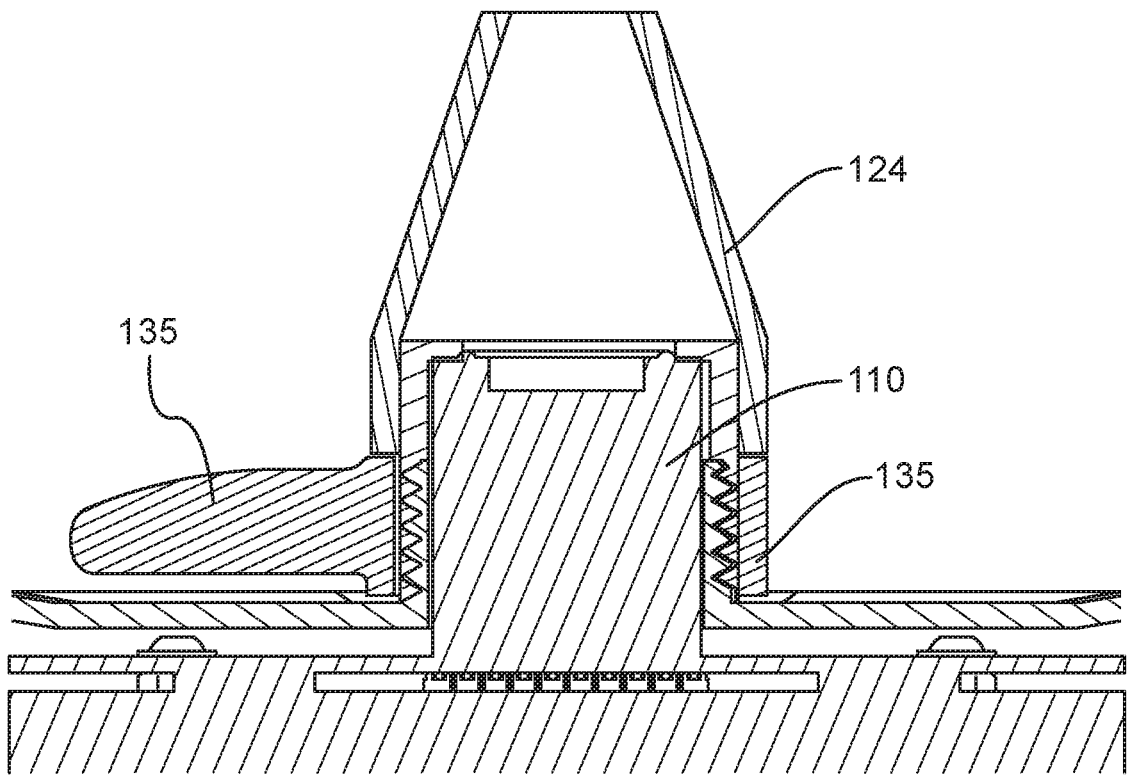
FIG. 4 is cross section view of an embodiment of the present invention showing the attachment of the base unit connection end (124) of the hollow rod to the base unit. The external on/off activation switch (135) can be seen.
Figure 5:
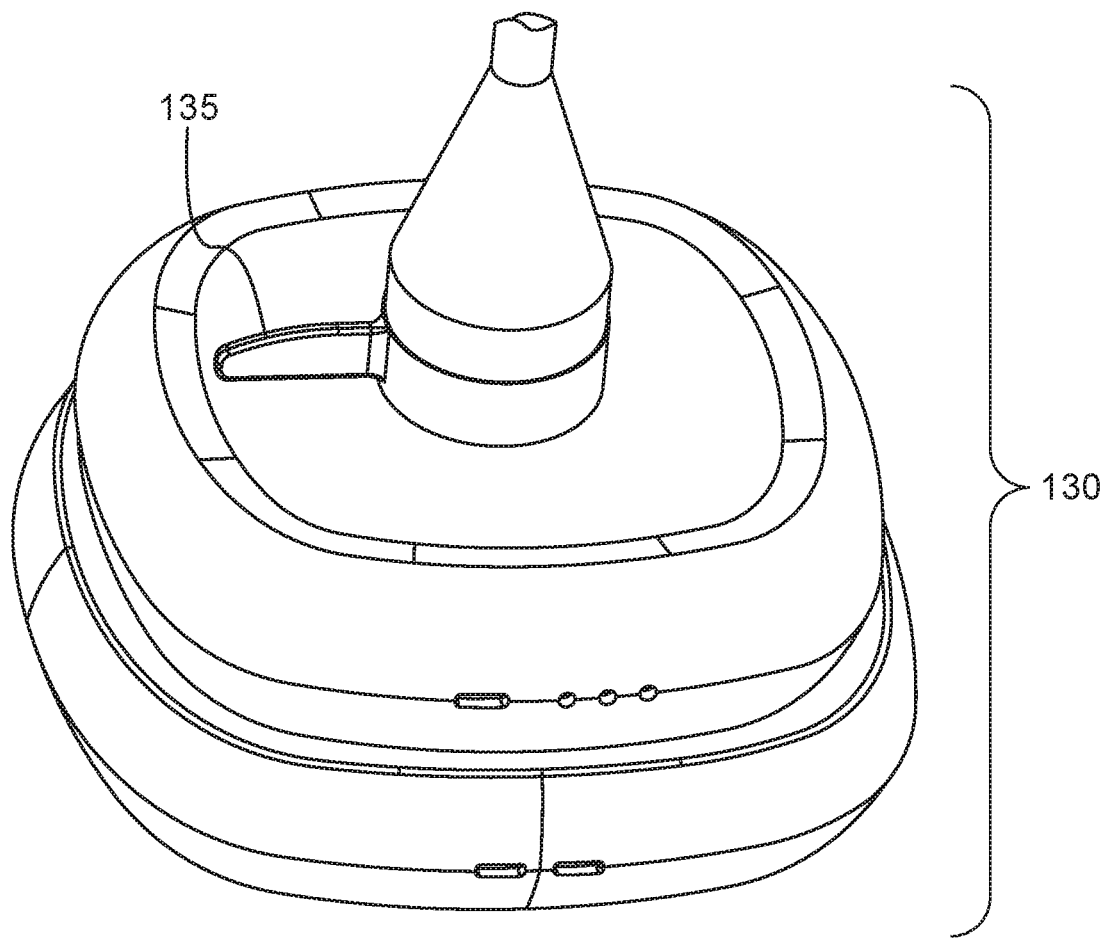
FIG. 5 is a top side view of an embodiment of the present invention showing the attachment of the base unit connection end (124) of the hollow rod to the base unit. The external on/off activation switch (135) activates the internal magnetic on/off switch.

Generally, the base end is 4 to 10 inches wide and 2 to 6 inches tall. Preferably, the base end is 6 to 9 inches wide and 3 to 5 inches tall. Most preferably, the base end is 7 to 8.5 inches wide and 3.5 to 5 inches tall. It should be recognized that the base unit width is sufficient to support the housing unit in an upright position when placed on a support such as a floor. See, for example, FIGS. 3 and 10. Preferably, the housing unit is made of a shock absorbing plastic. In certain embodiments the base unit is encased in a shock absorbing outer protective wrap/shell such as, for example, a silicone or rubber skin. Preferably, the protective wrap/shell is high visibility. Preferably, all hardware contained within the device is intrinsically safe (i.e., UL/IP67/CE/ATEX approved).

The base end of the device houses a data processor (e.g., mother board) which may also contain internal memory. The data processor is configured to execute instructions in the memory and to read and write data to and from the memory. Preferably, the base unit contains enough memory to capture, for example, at least 30 days of data.

The base end also contains a telemetry unit for sending data preferably via non-Wi-Fi or Bluetooth means. Telemetry based communications such as SMS/GMS can work without the internet on mobile devices allowing push notifications in cases where the gas concentration thresholds dip above and/or below a preset level. The device is capable of worldwide communication. The telemetry unit includes an antenna operably connected to a radio transmitter configured to wirelessly transmit data. The telemetry device can send data to cloud storage where it can be processed into visually presentable data and graphic depictions of the fumigation process. The telemetry unit can be adapted to transmit gas (e.g., Phosphine) ppm data at selected preset intervals e.g., every 2, 4, 6, 8, 12, 24 hours. To save on battery life, the device may operate in a sleep mode in between selected intervals. The device may be a configured for a higher power usage awake mode and a lower power usage sleep mode thus extending battery life.

The base unit also houses a power supply e.g., battery (133) which may be operably coupled to the memory chip, the data processor, the radio transmitter, on-off switch and the sensor. Preferably, as the base unit (130) is sealed the power supply is a battery capable of wireless charging. The base unit may also optionally contain an LED power indicator, an ON/OFF indicator and a charge indicator. Moreover, as the unit is sealed the base unit also contains a magnetic on/off switch operably coupled to the power supply. The magnetic switch allows the sealed device to be turned on/off without an external connection into the sealed housing. A FOB associated with the unit may be used to activate the magnetic on/off switch. A cleaning tool may also be included with the FOB to allow cleaning of the perforations in the sensor tip.

Figure 2:
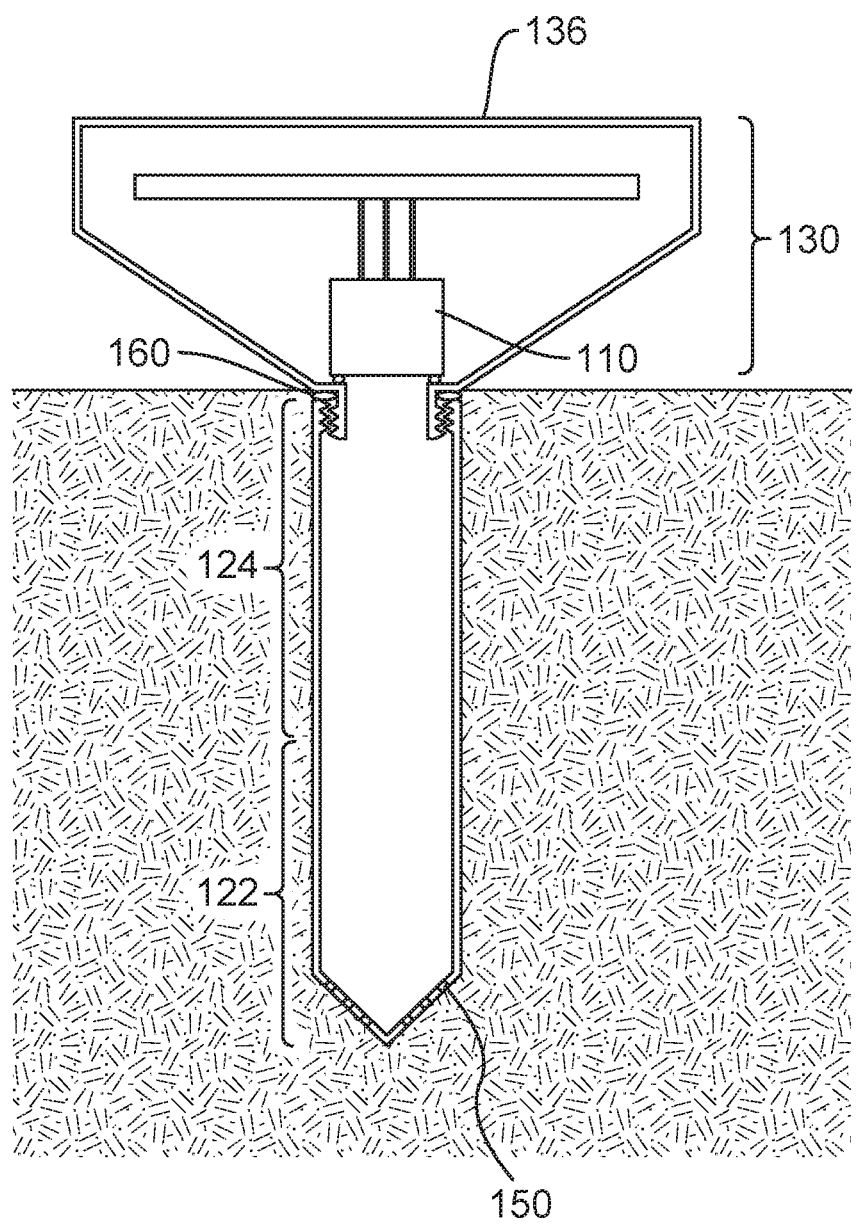
FIG. 2 depicts an embodiment of a gas monitoring device according to the present invention inserted with an enclosed environment containing stored commodities (not to scale).
Figure 7:
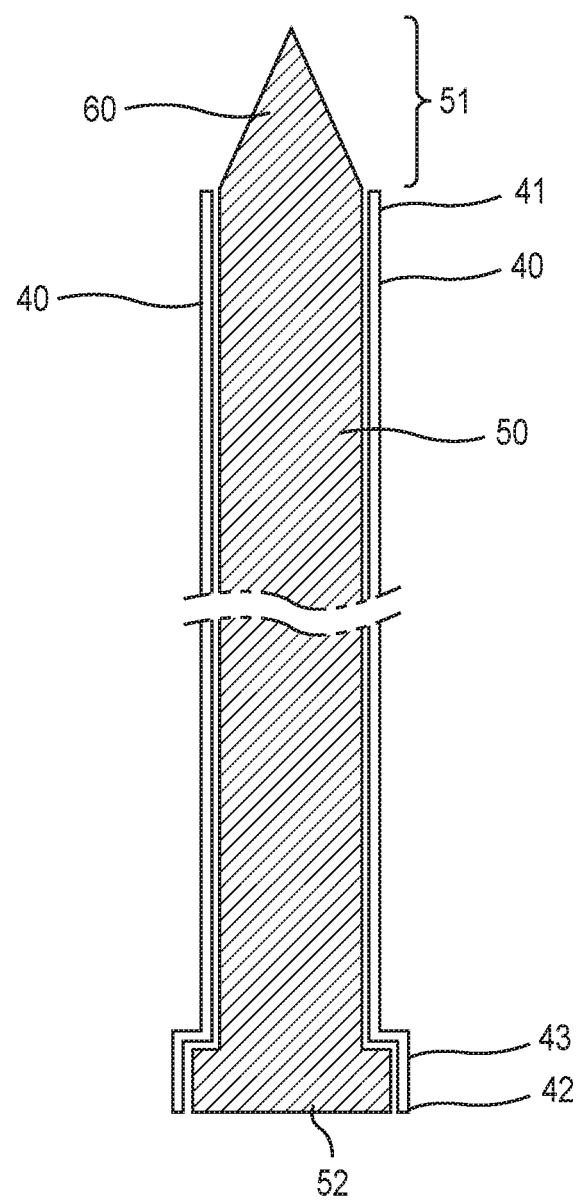
FIG. 7 depicts an embodiment of a two piece probe device according to the present invention.

FIG. 2 depict a method of monitoring the gas concentration within a fumigated commodity sample without the use of external mechanical sampling pumps. FIG. 2 depicts a device according to the present invention inserted into a commodity container. The force required to insert the device will depend on the commodity and how densely the commodity is packed within the container. Some commodities such as, for example, a densely packed tobacco may require a hammer to insert the device into the commodity. In some commodities such as, for example, corn kernels, the device can be placed with hand pressure alone. The outer surface of the device will be in direct contact with the commodity and therefore should be made of a recognized food contact material (FCM). FCMs must be sufficiently inert so that they do adversely affect consumer health nor influence the quality of the food. Preferably, the outer sleeve is stainless steel.
Probe Some embodiments are device is designed to be compatible with a 2-piece stainless probe unit used for the optional mode of inserting the device into a commodity. FIG. 7 depicts an embodiment of a two piece probe device according to the present invention. The probe will be a 2-piece stainless steel device approximately 20" to 30" in length. The outer sleeve (40) is a hollow tube with a tapered wall on one end and optionally a stainless steel round collar (43) on the second end of the outer sleeve (42). The tapered wall of the first end of the outer sleeve (41) allows the device to be more easily inserted into a commodity. The internal removable inner core (50) includes spike component (60) on the first end (51). The spike is typically slightly longer than the outer sleeve. The sharp pointed tip allows the spike to more easily penetrate the commodity. The inner core optionally contains a round collar welded on the other end. Once both pieces are inserted into the commodity packaging, the inside core will be removed leaving behind the hollow outer sleeve. The inside diameter of the outer sleeve will be just large enough to allow the insertion of the rod end of the measuring device.

Figure 8:
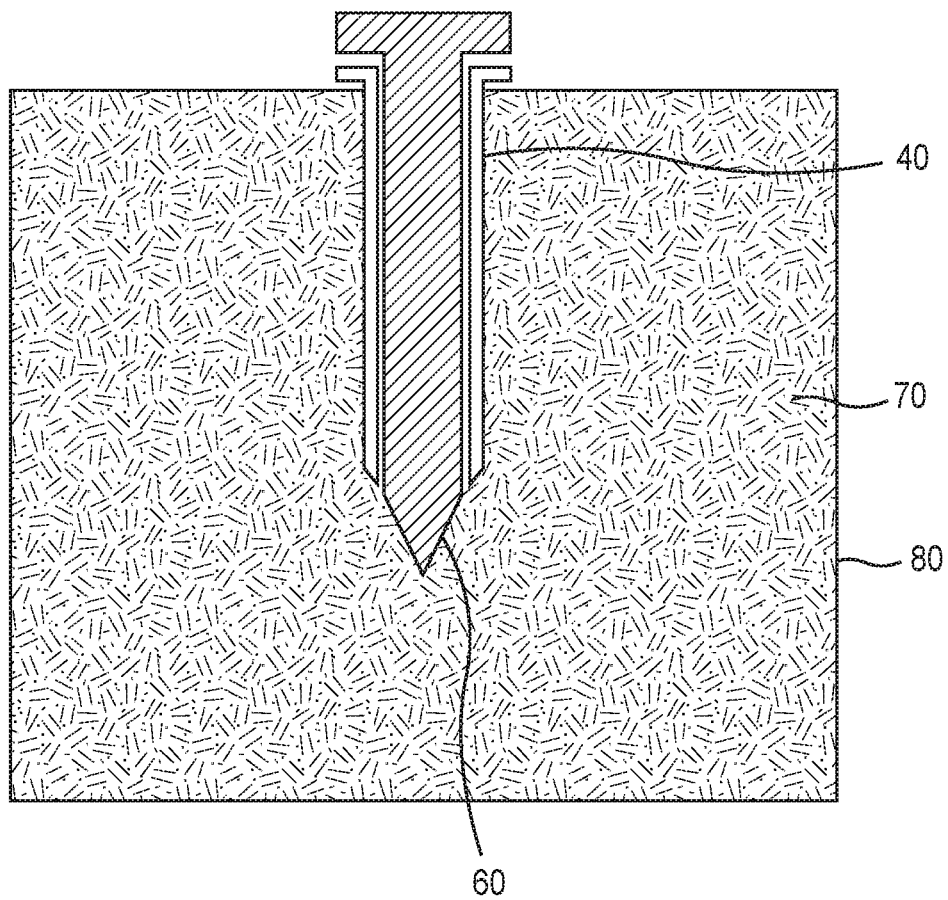
FIG. 8 depicts an embodiment in which a two piece probe device according to the present invention inserted into a commodity container.
Figure 9:
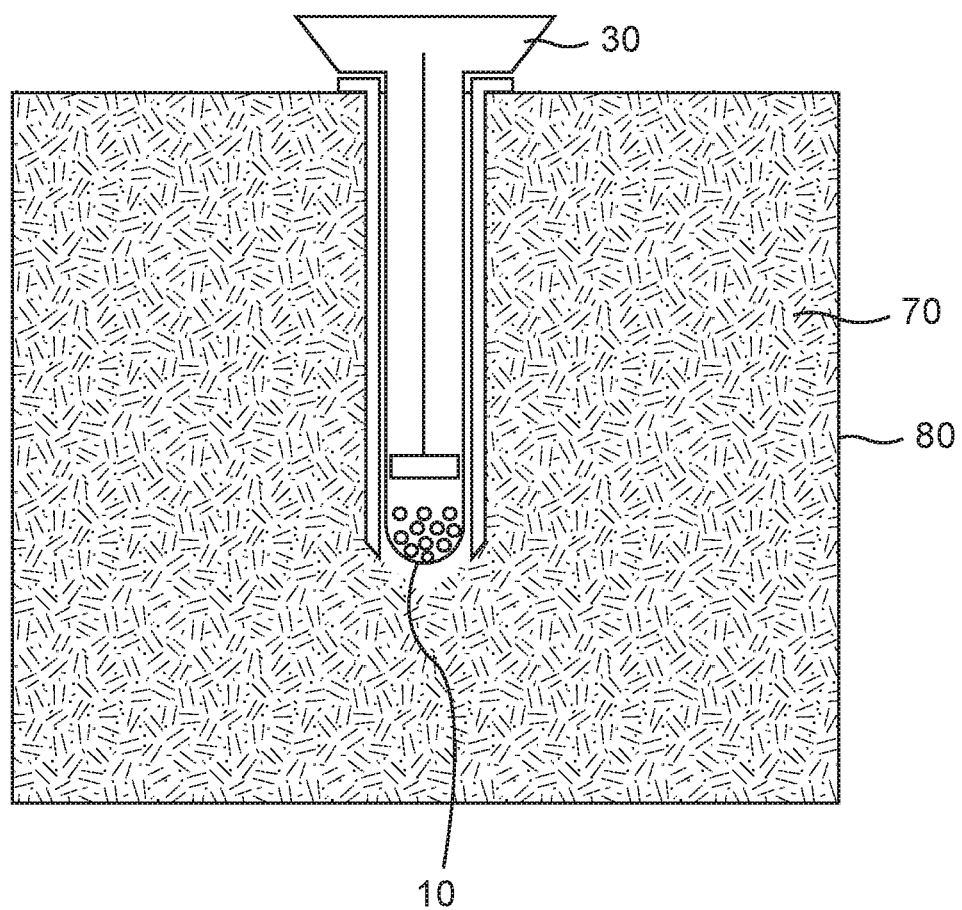
FIG. 9 depicts an embodiment in which the outer sleeve of the two piece probe device according to the present invention remains in the commodity container and an embodiment of a gas monitoring device according to the present invention is inserted into the outer sleeve.

FIGS. 8 and 9 depict a method of monitoring the gas concentration within a fumigated commodity sample without the use of external mechanical sampling pumps. FIG. 8 depicts a two piece probe device according to the present invention inserted into a commodity container. The force required to insert the two piece probe will depend on the commodity and how densely the commodity is packed within the container. Some commodities such as, for example, a densely packed tobacco may require a hammer to insert the two piece probe into the commodity. In some commodities such as, for example, corn kernels, the two piece probe can be placed with hand pressure alone. The outer sleeve of the two piece probe will be in direct contact with the commodity and therefore should be made of a recognized food contact material (FCM). FCMs must be sufficiently inert so that they do adversely affect consumer health nor influence the quality of the food. Preferably, the outer sleeve is stainless steel.

FIG. 9 depicts an embodiment in which the outer sleeve of the two piece probe device according to the present invention remains in the commodity container and a gas monitoring device according to the present invention is inserted into the outer sleeve. Preferably, the sensor tip (10) does not extend beyond the first end of the outer sleeve so as not to contact the commodity. In certain embodiments where the sensor tip does extend beyond the outer sleeve the sensor tip is be made of a recognized food contact material (FCM). The sensor is now positioned to monitor the gas concentrations within the inner areas of the insulated commodity without the need for problematic and unreliable external gas sampling.

End Use Software

The device includes software for fresh air calibration. Preferably, the unit zeros itself out when turned on. The device also includes calibration software which follow industry guidelines for gas concentration.

The base unit is adapted to transmit gas (e.g., Phosphine) ppm data at selected preset intervals e.g., every 2, 4, 6, 8, 12, 24 hours. The data, along with a time stamp, can be processed and accessed through a dashboard for viewing a graphical evaluation and/or reports of the fumigation concentration over time. Prior to fumigation, each job will be assigned a unique name (location and date) and each gas monitoring device is assigned a unique code (e.g., 4-digit unit ID). The unique location and unique device code associated with that fumigation are entered via the dashboard and named with a relevant name (e.g., warehouse number, silo number, container number, tarp number, etc.). During the fumigation, if a concentration received is below a preset ppm level, the software will send out an email and/or SMS notification to alert a predetermined group. Once the fumigation is over, the software will generate a post fumigation graph of phosphine concentrations in ppm vs. time in hours. The software allows access for guests invited to view the results of only that specific fumigation and the specific base units associated with it. Once the fumigation is over, the job will be finalized, and base units "released" from assignment.

Without further elaboration, it is believed that one skilled in the art can, using the preceding description, utilize the present invention to its fullest extent. The preferred specific embodiments are, therefore, to be construed as merely illustrative, and not limitative of the disclosure in any way whatsoever.

From the foregoing description, one skilled in the art can easily ascertain the essential characteristics of this invention and, without departing from the spirit and scope thereof, can make various changes and modifications of the invention to adapt it to various usages and conditions.

I claim:

1. A gas monitoring device comprising:
   a gas tight base unit containing a sensor, said base unit is detachably connected to an optional elongated hollow rod having a perforated tip end and a base unit connection end,
   a removable filter medium adjacent said sensor,
   wherein said base unit comprises said sensor, data processor, a telemetry unit, a battery with wireless charging and an internal on/off switch
   and wherein said telemetry unit transmits collected data via cellular data transfer mechanisms
   and wherein said internal on/off switch is activated magnetically.

2. A gas monitoring device according to claim 1, wherein said optional elongated hollow rod is between 12 to 36 inches long.

3. A gas monitoring device according to claim 1, wherein said optional elongated hollow is between 0.5 to 1 inch in diameter.

4. A gas monitoring device according to embodiment 1, wherein said base end is 4 to 10 inches wide and 2 to 6 inches tall.

5. A gas monitoring device according to embodiment 1, wherein said housing unit is made of a shock absorbing plastic.

6. The gas monitoring device according to claim 1, wherein said gas is phosphine and parts per million data is collected and transmitted via cellular data transfer mechanisms at preset intervals.

7. The gas monitoring device according to claim 1, wherein said telemetry unit sends data to cloud storage.

8. A gas monitoring device according to claim 1, wherein said device does not require external gas sampling pumps.

9. The gas monitoring device according to claim 1, wherein said cellular data transfer is via SMS/GMS.

10. The gas monitoring device according to claim 1, wherein said device works without the internet and provides push notifications in cases where the gas concentration thresholds dip above and/or below a preset level.

11. The gas monitoring device according to claim 1, wherein said device sends data to cloud storage where it can be processed into visually presentable data and graphic depictions of the fumigation process.

12. The gas monitoring device according to claim 1, wherein said device operates in a sleep mode in between selected preset intervals.

13. The gas monitoring device according to claim 1, wherein said device includes software for fresh air calibration.

14. The gas monitoring device according to claim 1, wherein collected data, along with a time stamp, is processed and accessed through a dashboard for viewing a graphical evaluation and/or reports of the fumigation concentration over time.

15. The gas monitoring device according to claim 1, wherein said filter is located with the base unit connection end of said optional hollow rod.

16. The gas monitoring device according to claim 1, wherein said filter sits above said sensor.

17. A method of monitoring the gas concentration within a fumigated space comprising placing a bottom side of the base unit of a gas monitoring device according to claim 1 on a solid support surface wherein the perforated end of said elongated hollow rod is located above the base unit and is exposed to the ambient air within the fumigated space.

18. A method according to claim 17, wherein said gas is phosphine and parts per million data is collected and transmitted via telemetry based communication unit at preset intervals.

* * * * *